United States Patent [19]

Nishiyama et al.

[11] 4,241,213

[45] Dec. 23, 1980

[54] PROCESS FOR PRODUCING 2-CHLORO-5-TRICHLOROMETHYL PYRIDINE

[75] Inventors: Ryuzo Nishiyama, Takatsuki; Kanichi Fujikawa, Kusatsu; Isao Yokomichi, Moriyama; Rikuo Nasu; Takao Awazu, both of Kyoto; Junichi Kawashima, Shiga, all of Japan

[73] Assignee: Ishihara Sangyo Kaisha Limited, Osaka, Japan

[21] Appl. No.: 75,022

[22] Filed: Sep. 13, 1979

[30] Foreign Application Priority Data

Sep. 22, 1978 [JP] Japan ............................. 53/115820

[51] Int. Cl.$^3$ ............................................ C07D 213/26
[52] U.S. Cl. .................................................. 546/345
[58] Field of Search ............................................ 546/345

[56] References Cited

U.S. PATENT DOCUMENTS

| 3,412,095 | 11/1968 | Clark | 546/345 |
| 3,420,833 | 1/1969 | Taplin | 260/283 |

*Primary Examiner*—Alan L. Rotman
*Attorney, Agent, or Firm*—Oblon, Fisher, Spivak, McClelland & Maier

[57] ABSTRACT

2-Chloro-5-trichloromethyl pyridine is produced by reacting β-picoline with chlorine in a gaseous phase at 300° to 500° C. in the presence of an inert diluent of nitrogen, a halogenated methane, a halogenated ethane a halogenated ethylene or a mixture thereof. 2-Chloro-5-trichloromethyl pyridine is useful as an intermediate for medicines, agricultural chemicals, dyes especially herbicides.

6 Claims, No Drawings

PROCESS FOR PRODUCING 2-CHLORO-5-TRICHLOROMETHYL PYRIDINE

BACKGROUND OF THE INVENTION:

1. FIELD OF THE INVENTION:

The present invention relates to a novel process for producing 2-chloro-5-trichloromethyl pyridine by reacting β-picoline with chlorine in a gaseous phase. 2-Chloro-5-trichloromethyl pyridine is useful as an intermediate for medicines, agricultural chemicals and dyes especially herbicides.

2. DESCRIPTION OF THE PRIOR ARTS:

It has been proposed to produce 2-chloro-5-trichloromethyl pyridine by diazotizing 2-amino-5-methyl pyridine and then brominating it to obtain 2-bromo-5-methyl pyridine and dissolving it in carbon tetrachloride and chlorinating it with chlorine in a liquid phase under irradiating ultraviolet rays.

However, this process has disadvantages that 2-amino-5-methyl pyridine as the starting material is expensive and complicated reaction steps are required and a reaction time is long.

The inventors have considered to carry out a gas phase chlorination of β-picoline as an economical starting material. However, it has been considered to be difficult to succeed in a chlorination of β-picoline so as to convert methyl group at β-position to trichloromethyl group, more difficult to succeed in a chlorination of β-picoline to di- or tri-chloromethyl group than monochloromethylation. Thus, an industrial success has not been expected.

For example, in HELVETICA CHIMICA ACTA, Vol. 59, Fase 1, Nr. 19–20, 1976 there is the description that the chlorination of methyl group of β-picoline is difficult, and 2,6-dichloro-3-halogenated methyl pyridine can be obtained from α-methylene glutaronitrile. In U.S. Pat. No. 3,412,095, there is the description that β-picoline is chlorinated in a gaseous phase in the presence of steam to obtain monochloromethyl compound, however there is no description that trichloromethyl compound is obtained. Even though the chlorination is further carried out by increasing proportion of chlorine by this process, only nicotinic acid is obtained. It has been proposed to produce 2-chloro-5-trichloromethyl pyridine by dissolving β-picoline in carbon tetrachloride and introducing chlorine gas in the solution under irradiating ultraviolet rays. However, the reaction time is too long and the yield is too low as several percent and this is not suitable for industrial purpose.

SUMMARY OF THE INVENTION:

It is an object of the present invention to provide a process for producing 2-chloro-5-trichloromethyl pyridine by using β-picoline as the economical starting material in high yield. Another object of the present invention is to provide an industrially advantageous process for producing 2-chloro-5-trichloromethyl pyridine.

The foregoing and other object of the present invention have been attained by providing a process for producing 2-chloro-5-trichloromethyl pyridine by reacting β-picoline with chlorine in a gaseous phase at 300° to 500° C. in the presence of an inert diluent of nitrogen, a halogenated methane, a halogenated ethane, a halogenated ethylene or a mixture thereof.

DETAILED DESCRIPTION OF THE PREFERRED EMBODIMENTS:

Various chlorinations of β-picoline have been studied. As a result, it has been found the fact that a radical reaction of β-picoline with chlorine performs for a short time in a gas phase chlorination of β-picoline under a specific condition so as to substitute subsequently hydrogen atoms to chlorine atoms in a side chain chlorination of β-picoline whereby methyl group is converted into trichloromethyl group. On the other hand, in a nuclear chlorination of β-picoline, hydrogen atom at 6-position is substituted to chlorine atom.

In accordance with the process of the present invention, 2-chloro-5-trichloromethyl pyridine is produced by reacting β-picoline with chlorine in a gaseous phase at 300° to 500° C. in a residence time of 0.5 to 60 seconds in the presence of an inert diluent of nitrogen, a halogenated methane, a halogenated ethane, a halogenated ethylene or a mixture thereof.

Suitable halogenated methanes, halogenated ethanes and halogenated ethylenes include carbon tetrachloride, trichloroethylene, tetrachloroethylene, difluorotetrachloroethane, trichlorotrifluoroethane, etc.

The advantages of the process of the present invention are as follows.

(1) 2-Chloro-5-trichloromethyl pyridine can be obtained in high yield of 30 to 60% based on β-picoline in the process of the present invention.

(2) 2-Chloro-5-trichloromethyl pyridine can be produced with industrial advantages in the process of the present invention because the starting material is economical and the reaction step is simple and the reaction time is short.

(3) The unreacted starting material, the inert diluent and the chlorinated products which are not chlorinated to form the object compound can be advantageously separated recovered and recycled to the chlorinating step.

The detail of the present invention will be further illustrated.

In the process of the present invention, β-picoline as the starting material and chlorine are usually separately fed into a reactor with an inert diluent of nitrogen, a halogenated methane, a halogenated ethane, a halogenated ethylene or a mixture as a carrier so as to use them for the reaction.

These materials are usually fed into the reactor after preheating. For example, in the feeding of β-picoline as the starting material, β-picoline is fed into an inert diluent gas heated at high temperature or a solution of β-picoline in an inert diluent liquid is heated to be vaporized.

In the process of the present invention, the reaction can be carried out in the presence of a filler such as a porous material e.g. silica, alumina, silicon carbide etc.; ceramics; glass; and a mixture thereof. The filler is not always needed.

In the industrial process, the filler is used as a fixed bed or a fluidized bed in the reactor so as to improve its reaction efficiency. For example, in the fluidized bed system, a vertical reactor having the fluidized bed of the filler is employed and preheated starting materials are fed through the bottom of the reactor to fluidized the filler during the reaction.

The inert diluent has the functions for controlling combustion, carbonization and formation of tar by-product as those of the conventional gas phase chlorination and also has the function for producing the object compound in stable. It is preferable to use a mixture of nitrogen and one of halogenated methanes, halogenated ethanes and halogenated ethylenes in an industrial process.

The proportion of the inert diluent is dependent upon the condition of the reaction and is not critical and is usually in a range of 3 to 70 preferably 10 to 30 mole per 1 mole of β-picoline.

The proportion of chlorine is not critical and is usually in a range of 4 to 8 mole per 1 mole of β-picoline.

The reaction temperature is usually in a range of 300° to 500° C. preferably 330° to 470° C. When it is too low, the reaction efficiency is low, whereas when it is too high, the decomposing reaction is disadvantageously caused.

The residence time of the reaction mixture in the reaction zone is usually in a range of 0.5 to 60 seconds preferably 1 to 15 seconds.

The reaction product obtained by the reaction of the present invention include 2-chloro-5-trichloromethyl pyridine as the object compound in high proportion and also other products of 2-chloro-3-trichloromethyl pyridine, 2,6-dichloro-3-trichloromethyl pyridine, 3-trichloromethyl pyridine, 2-chloro-3-dichloromethyl pyridine, 2-chloro-5-dichloromethyl pyridine, 2,6-dichloro-3-dichloromethyl pyridine and 3-dichloromethyl pyridine.

In the reaction of β-picoline with chlorine of the present invention, the radical reaction is sequentially performed so as to substitute hydrogen atoms by chlorine atoms. Thus, various chlorinated compounds are produced. At the initiation of the reaction 3-monochloromethyl pyridine is mainly produced and then, the production of 3-dichloromethyl pyridine is increased and then the production of 2-chloro-5-dichloromethyl pyridine, 2-chloro-3-dichloromethyl pyridine, and 3-trichloromethyl pyridine is increased and finally the production of 2-chloro-5-trichloromethyl pyridine as the object compound is increased.

With regard to the chlorinated compounds obtained from β-picoline during the reactions, lower chlorinated products are thermally less stable. When the reaction mixture is remained in a high temperature zone for a long time, side reactions such as carbonization and combustion are easily caused. Therefore, it is necessary to control the residence time carefully. Moreover, it is necessary to select suitable ratios, amounts and flow rates of the starting materials and the inert diluent and a reaction temperature as the condition of the chlorination. When steam is used as a diluent, the pyridine compounds having trichloromethyl group produced during the reactions are converted into nicotinic acids by their hydrolysis and the object compound is not obtained.

In accordance with the process of the present invention, the object compound can be obtained without a decomposition or a interference during the reaction only by using the inert diluent.

A gaseous mixture including 2-chloro-5-trichloromethyl pyridine as a main component and other chlorinated products, the inert diluent, hydrogen chloride and the unreacted chlorine is discharged from the reactor. Mixture including 2-chloro-5-trichloromethyl pyridine can be separated as a liquid by a desired cooling apparatus and a condensing apparatus and can be purified by the conventional purifying processes such as a distillation, an extraction and a crystallization to obtain the object compound having high purity. For example, 2-chloro-5-trichloromethyl pyridine is obtained in high yield of 30 to 60% based on β-picoline.

The unreacted starting materials, the inert diluent and the chlorinated products which are not chlorinated to form the object compound can be separated, recovered and recycled to the chlorinating step.

The present invention will be illustrated by certain examples and references which are provided for purposes of illustration only and are not intended to be limiting the present invention.

EXAMPLE 1

A reaction tube made of glass having a diameter of 4 cm and a length of 50 cm equipped with thermocouples was employed. Two gas inlet pipes were inserted into the reaction tube through a preheater. The reaction tube was covered with an electric heater and an insulating material so as to externally control the temperature and was placed in slant.

One gas inlet pipe was used for feeding dried chlorine gas and the other gas inlet pipe was used for feeding a gas mixture prepared by heating and vaporizing, a carbon tetrachloride solution of β-picoline in nitrogen gas flow. A receiver having a condenser for collecting the discharged gas was equipped at the outlet of the reaction tube.

Through the reaction tube, 11.2 g. of β-picoline, 106 ml. of carbon tetrachloride, 19 g. of nitrogen and 47.6 g. of chlorine were fed during 30 minutes to carry out a gas phase reaction at 400° C. The residence time of the gases in the reaction tube was about 9 seconds.

The liquid products collected in the receiver was washed with a dilute aqueous solution of ammonia and dried over anhydrous sodium sulfate. Carbon tetrachloride was distilled off under a reduced pressure to obtain 24.6 g. of an oily product. According to an analysis of the oily product, it was found to contain 0.2 wt. % of 3-dichloromethyl pyridine, 1.8 wt. % of 3-trichloromethyl pyridine, 74.4 wt. % of 2-chloro-5-trichloromethyl pyridine, 12.7 wt. % of 2-chloro-3-trichloromethyl pyridine and 6.2 wt. % of 2,6-dichloro-3-trichloromethyl pyridine.

The oily product was purified by a column chromatography to obtain 12.1 g. of 2-chloro-5-trichloromethyl pyridine.

EXAMPLE 2

A bead silica was filled in the reaction tube used in the process of Example 1 and 22.4 g. of β-picoline, 152 ml. of carbon tetrachloride, 27 g. of nitrogen and 85.2 g. of chlorine were fed through the reaction tube during 2.5 hours to carry out a gas phase reaction at 450° C. for a residence time of about 5.5 seconds.

In accordance with the process of Example 1, the discharged gas was treated to obtain 51 g. of an oily product having substantially the same components and the oily product was purified to obtain 27 g. of 2-chloro-5-trichloromethyl pyridine.

EXAMPLE 3

A reaction tube made of quartz having a diameter of 3 cm and a length of 210 cm equipped with thermocouples was employed. Two gas inlet pipes were inserted into the reaction tube through a preheater. The reaction tube was covered with an electric heater and an insulating material so as to externally control the temperature and was placed in slant.

One gas inlet pipe was used for feeding dried chlorine gas preheated at 200° C. and the other gas inlet pipe was used for feeding a gas mixture prepared by heating and vaporizing a carbon tetrachloride solution of β-picoline at 200° to 250° C. in nitrogen gas flow. A receiver having a condenser for collecting the discharged gas was equipped at the outlet of the reaction tube.

The carbon tetrachloride solution of β-picoline was fed at 13 ml/min. and chlorine gas was fed at 2.8 N liter/min. and nitrogen gas was fed at 8.0 N liter/min. (molar ratios of β-picoline: $CCl_4:Cl_2:N_2 = 1:5:5.6:15.9$). A gas phase reaction was carried out at 430° C. for a residence time of about 2.5 seconds in the reaction tube. After the reaction for about 2 hours, the condensed reaction mixture was analyzed to find 58 wt. % of 2-chloro-5-trichloromethyl pyridine, 18 wt. % of 2-chloro-3-trichloromethyl pyridine; 15 wt. % of 2,6-dichloro-3-trichloromethyl pyridine and 9% of the other products of 3-trichloromethyl pyridine, 2-chloro-3-dichloromethyl pyridine, 2-chloro-5-dichloromethyl pyridine, and 2,6-dichloro-3-dichloromethyl pyridine, etc. The reaction mixture was washed with a dilute aqueous solution of sodium hydroxide. Carbon tetrachloride was distilled off under a reduced pressure and the product was distilled and recrystallized to obtain 207 g. of 2-chloro-5-trichloromethyl pyridine having a purity of 96.4% in the yield of 30.6% based on β-picoline.

EXAMPLE 4

Through the reaction tube used in the process of Example 3, the difluorotetrachloroethane solution of β-picoline was fed at 1.3 ml/ min.; hlorine gas was fed at 200 ml/min. nitrogen gas was fed at 600 ml/min. (molar ratios of β-picoline: $C_2Cl_4F_2:Cl_2:N_2 = 1:5:5.6:15.9$). A gas phase reaction was carried out at 350° C. for a residence time of about 12 seconds during 6 hours.

In accordance with the process of Example 3, the reaction mixture was collected and purified to obtain 50.3 g. of 2-chloro-5-trichloromethyl pyridine in the yield of 35% based on β-picoline.

We claim:

1. In a process for producing 2-chloro-5-trichloromethyl pyridine by reacting β-picoline with chlorine, an improvement characterized by reacting β-picoline with chlorine in a gaseous phase at 300° to 500° C. in the presence of an inert diluent selected from the group consisting of nitrogen, halogenated methanes, halogenated ethanes, halogenated ethylenes and mixtures thereof.

2. A process according to claim 1 wherein a residence time in a reaction zone is in a range of 0.5 to 60 seconds.

3. A process according to claim 1 wherein said inert diluent is a mixture of nitrogen and one of halogenated methanes, halogenated ethanes and halogenated ethylenes.

4. A process according to claim 1 wherein said reaction temperature is in a range of 330° to 470° C.

5. A process according to claim 1 wherein a molar ratio of chlorine to β-picoline is in a range of 4 to 8.

6. A process according to claim 1 wherein a molar ratio of the inert diluent to β-picoline is in a range of 3 to 70.

* * * * *